United States Patent
Heikenfeld

(10) Patent No.: US 11,369,349 B2
(45) Date of Patent: Jun. 28, 2022

(54) WEARABLE SWEAT BIOSENSING DEVICES WITH ACTIVE SWEAT SAMPLE COUPLING

(71) Applicant: University Of Cincinnati, Cincinnati, OH (US)

(72) Inventor: Jason C. Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 124 days.

(21) Appl. No.: 16/468,464

(22) PCT Filed: Dec. 20, 2017

(86) PCT No.: PCT/US2017/067495
§ 371 (c)(1),
(2) Date: Jun. 11, 2019

(87) PCT Pub. No.: WO2018/125695
PCT Pub. Date: Jul. 5, 2018

(65) Prior Publication Data
US 2020/0077988 A1    Mar. 12, 2020

Related U.S. Application Data

(60) Provisional application No. 62/439,672, filed on Dec. 28, 2016.

(51) Int. Cl.
*A61B 10/00* (2006.01)
*A61B 5/145* (2006.01)
(Continued)

(52) U.S. Cl.
CPC ........ *A61B 10/0064* (2013.01); *A61B 5/1477* (2013.01); *A61B 5/14517* (2013.01); *A61B 5/14546* (2013.01); *A61B 5/6833* (2013.01)

(58) Field of Classification Search
CPC ............ A61B 10/0064; A61B 5/14516; A61B 5/1477; A61B 5/14517–14521;
(Continued)

(56) References Cited

U.S. PATENT DOCUMENTS

| 5,050,604 A | 9/1991 | Reshef et al. |
| 10,368,847 B2 * | 8/2019 | Heikenfeld .......... A61B 5/1491 |

(Continued)

FOREIGN PATENT DOCUMENTS

| WO | WO-2009137415 A2 * | 11/2009 | ........ B01L 3/502715 |
| WO | WO-2016049019 A1 * | 3/2016 | .......... A61B 5/4266 |

(Continued)

OTHER PUBLICATIONS

Fei He, Jeff Grimes, Samuel D. Alcaine, Sam R. Nugen "A hybrid paper and microfluidic chip with electrowetting valves and colorimetric detection," Analyst, 139, 3002-3008 (Year: 2014).*

(Continued)

*Primary Examiner* — Eric F Winakur
*Assistant Examiner* — Alice Ling Zou
(74) *Attorney, Agent, or Firm* — Wood Herron & Evans LLP

(57) ABSTRACT

A device (100) for sensing a first analyte in sweat on skin includes an analyte-specific sensor (120) for sensing the first analyte and an active sweat coupling component (130) for transporting at least one sweat sample inside the device (100) and into fluid communication with the analyte-specific sensor (120). A method of sensing a first analyte in sweat on skin includes actively transporting at least one sweat sample into fluid communication with an analyte-specific sensor (120) for sensing the first analyte using an active sweat coupling component (130) and sensing the first analyte using the analyte-specific sensor (120).

21 Claims, 3 Drawing Sheets

(51) Int. Cl.
*A61B 5/1477* (2006.01)
*A61B 5/00* (2006.01)

(58) Field of Classification Search
CPC ............ A61B 5/14546; A61B 5/14532; A61B 5/1468; A61B 5/1486; A61B 5/6801; A61B 5/683; A61B 5/6832; A61B 5/6833; B01L 2400/046; B01L 2400/0427; G01N 27/44791
See application file for complete search history.

(56) References Cited

U.S. PATENT DOCUMENTS

| | | |
|---|---|---|
| 2003/0191376 A1 | 10/2003 | Samuels et al. |
| 2007/0027383 A1 | 2/2007 | Peyser et al. |
| 2007/0241068 A1* | 10/2007 | Pamula ............ B01L 3/502715 210/806 |
| 2010/0063372 A1 | 3/2010 | Potts et al. |
| 2015/0112164 A1 | 4/2015 | Heikenfeld et al. |

FOREIGN PATENT DOCUMENTS

| | | | | |
|---|---|---|---|---|
| WO | WO-2017070640 A1 * | 4/2017 | ......... | A61B 5/14546 |
| WO | WO-2018067412 A1 * | 4/2018 | ......... | A61B 5/14517 |

OTHER PUBLICATIONS

Frieder Mugele and Jean-Christophe Baret, "Electrowetting: from basics to applications" J. Phys,: Condens. Matter, 17, R705-R774 (Year: 2005).*
A. Nisar, Nitin Afzulpurkar, Banchong Mahaisavariya, Adison Tuantranont, "MEMS-based micropumps in drug delivery and biomedical applications," Sensors and Actuators B, 130, 917-942 (Year: 2008).*
Vijay Srinivasan, Vamsee K. Pamula, and Richard B. Fair; "An integrated digital microfluidic lab-on-a-chip for clinical diagnostics on human physiological fluids," 2004, Lab Chip, 4, 310-315 (Year: 2004).*
International Search Report in International Patent Application No. PCT/US2017/067495, dated Mar. 1, 2018, 2 pgs.
Written Opinion in International Patent Application No. PCT/US2017/067495, dated Mar. 1, 2018, 6 pgs.

* cited by examiner

WEARABLE SWEAT BIOSENSING DEVICES WITH ACTIVE SWEAT SAMPLE COUPLING

BACKGROUND

Sweat sensing technologies have enormous potential for applications ranging from athletics, to neonatology, to pharmacological monitoring, to personal digital health, to name a few applications. Sweat contains many of the same biomarkers, chemicals, or solutes that are carried in blood and can provide significant information enabling one to diagnose ailments, health status, toxins, performance, and other physiological attributes even in advance of any physical sign. Furthermore, sweat itself, the action of sweating, and other parameters, attributes, solutes, or features on, near, or beneath the skin can be measured to further reveal physiological information.

Biosensing using sweat has many drawbacks and limitations. A need exists for improved systems and methods for generating, efficiently collecting, and accurately sensing sweat.

SUMMARY OF THE INVENTION

An aspect of the disclosed invention provides a device for sensing at least a first analyte in sweat on skin. In an embodiment, a device includes at least one analyte-specific sensor for sensing a first analyte in sweat and at least one active sweat coupling component for transporting at least one sweat sample from skin into the device in a manner that brings the at least one sweat sample into fluid communication with the analyte-specific sensor.

Another aspect of the disclosed invention provides a method of sensing at least a first analyte in sweat on skin. In an embodiment, a method includes actively transporting at least one sweat sample into fluid communication with an analyte-specific sensor for sensing the first analyte using an active sweat coupling component and sensing the first analyte using the analyte-specific sensor.

The objects and advantages of the disclosed invention will be further appreciated in light of the following detailed descriptions and drawings.

DETAILED DESCRIPTION OF THE INVENTION

Reference throughout this specification to "one embodiment" or "an embodiment" means that a particular feature, structure, material, or characteristic described in connection with the embodiment is included in at least one embodiment of the invention, but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one."

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Certain embodiments of the disclosed invention show sensors as simple individual elements. It is understood that many sensors require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sample volume sensor; a sample generation rate sensor; and a solute generation rate sensor. Certain embodiments of the disclosed invention show sub-components of what would be sensing devices with more sub-components needed for use of the device in various applications, which are known (e.g., a battery), and for purposes of brevity and focus on inventive aspects, such components are not explicitly shown in the diagrams or described in the embodiments of the disclosed invention. As a further example, many embodiments of the disclosed invention could benefit from mechanical or other means known to those skilled in wearable devices, patches, bandages, and other technologies or materials affixed to skin, to keep the devices or sub-components of the skin firmly affixed to skin or with pressure favoring constant contact with skin or conformal contact with even ridges or grooves in skin, and are included within the scope of the disclosed invention.

Figure 1A:
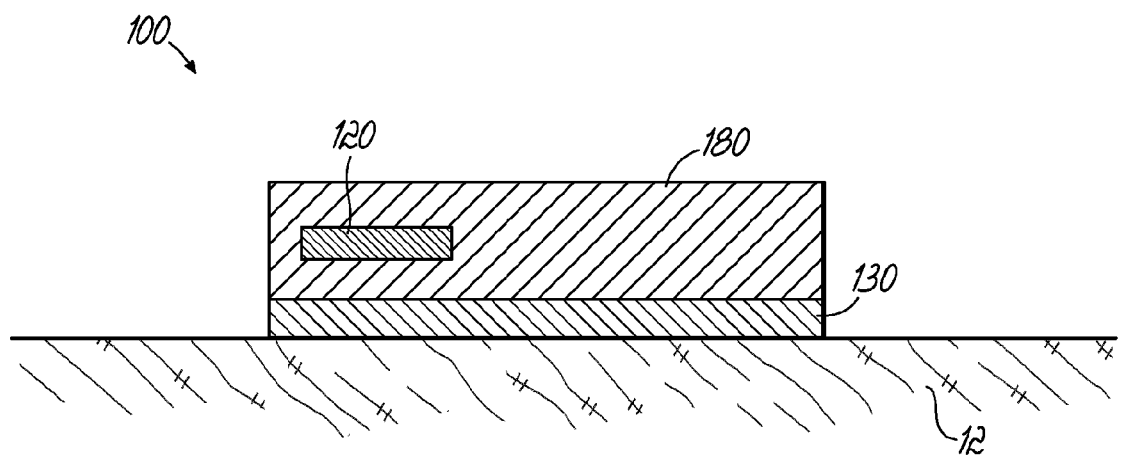
FIG. 1A is a cross-sectional view of a device according to an embodiment of the disclosed invention.

With reference to FIG. 1A, in an embodiment of the disclosed invention, a device 100 includes a lab-on-chip component 180 containing at least one analyte-specific sensor 120. The lab-on-chip component 180 may be any type of lab-on-chip system that utilizes a combination of microfluidics and sensing capabilities to sense at least one specific analyte in a biofluid, such as sweat. Numerous possible examples are known by those skilled in the art. The sensor 120 may be, without limitation, an ion-selective electrode for potassium, an enzymatic sensor for glucose, an electrochemical aptamer sensor for cortisol, or a colorimetric sensor assay for albumin. While the embodiments herein are described relative to transporting and sensing sweat, embodiments of the disclosed invention apply to other biofluid applications, such as those involving blood, interstitial fluid, saliva, or tears.

The device 100 further includes a sweat coupling component 130 that enables fluidic coupling and/or introduction of sweat from skin 12 into the lab-on-chip component 180.

In some cases, e.g., where the lab-on-chip component 180 transports fluid via single-plate electrowetting, such sweat coupling components 130 are incapable of pulling fluid into the lab-on-chip component 180 by passive transport, such as wicking, and require the sweat sample to be introduced at a significant input pressure to allow proper functioning. Although sweat generation can provide positive pressures of sweat that can be pushed into a device, such operation requires an adequate pressure seal against the skin surface, which may be difficult to achieve and maintain, and which may increase contamination coming from the skin surface as sweat is in contact with the skin surface for longer periods of time. This difficultly generally becomes greater at low sweat generation rates (e.g., less than 1 nL/min/gland). In general, embodiments of the disclosed invention therefore provide at least one sweat coupling component 130, which includes at least one active (i.e., not passive) mechanism for introducing a sweat sample into the lab-on-chip component 180 with a positive pressure. In other words, the sweat coupling component 130 does not passively transport sweat due to, for example, the wicking properties of the sweat coupling component 130. Rather, the sweat coupling component 130 provides an active force or power (e.g., electrical, mechanical, thermal, etc.) to drive transport of sweat.

Figure 1B:
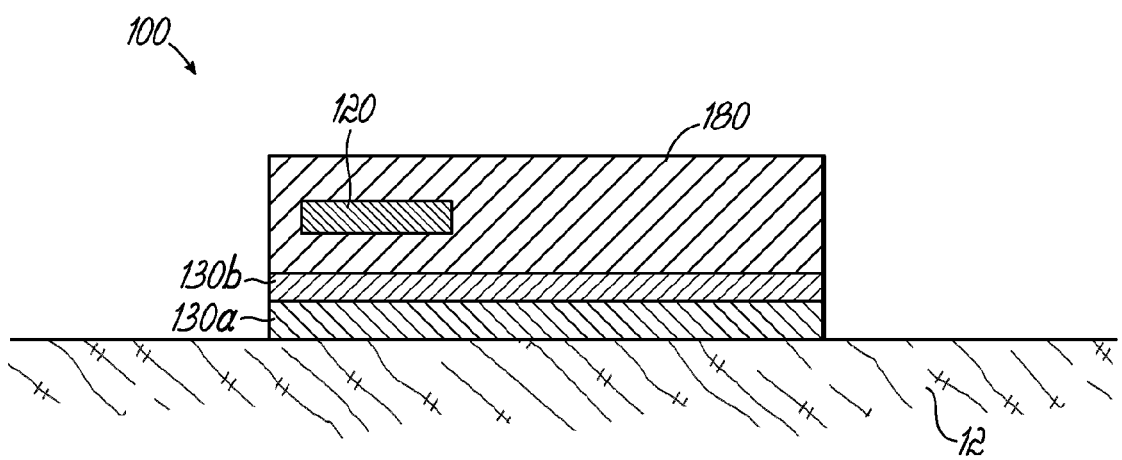
FIG. 1B is a cross-sectional view of a device according to an embodiment of the disclosed invention.

With reference to FIG. 1B, in an embodiment of the disclosed invention, the device 100 further includes a sweat coupling component with multiple sub-components 130a, 130b, both of which enable fluid coupling and/or introduction of sweat from the skin 12 into the lab-on-chip component 180. The sub-components 130a, 130b may be different or the same, e.g., for purposes such as building up additional pressure or increasing the flow rate for introduction of sweat sample into the lab-on-chip component 180.

Figure 2A:
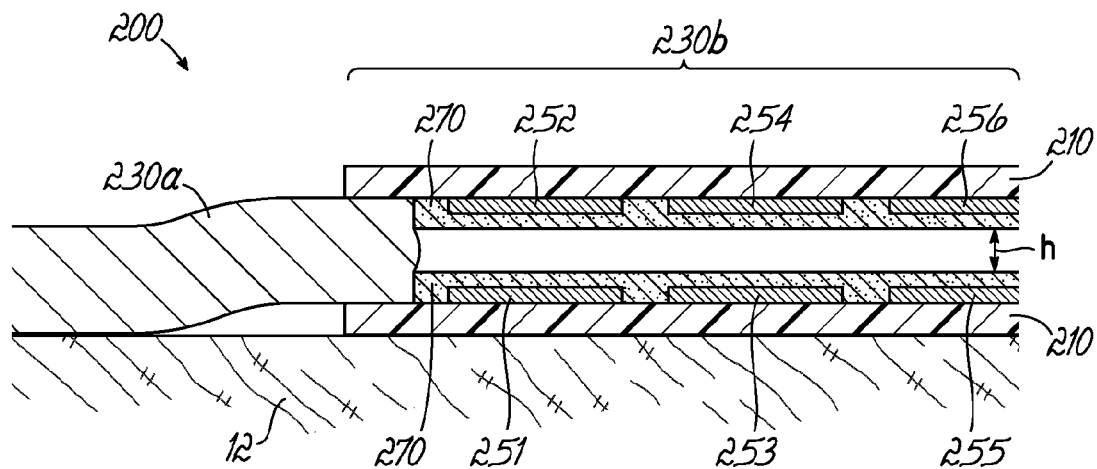
FIG. 2A is a cross-sectional view of a device according to an embodiment of the disclosed invention.
Figure 2B:
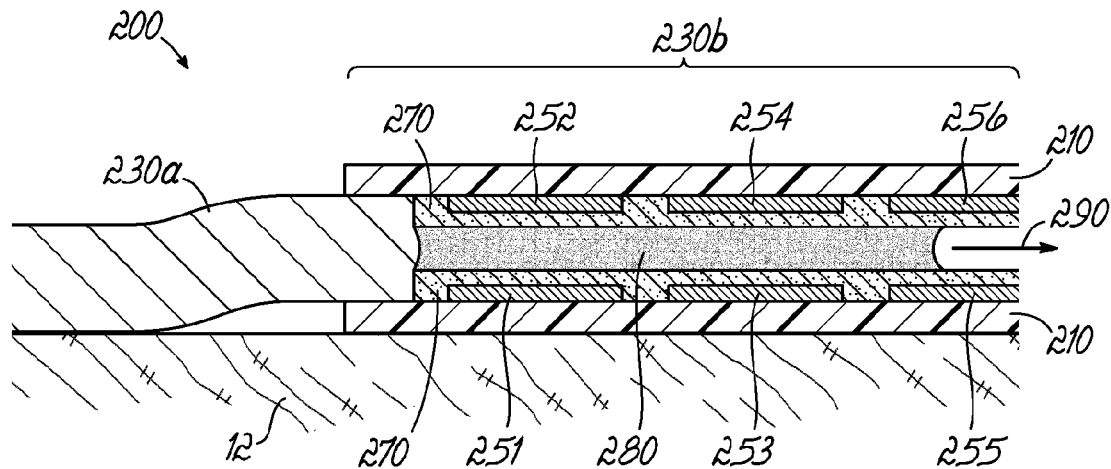
FIG. 2B is a cross-sectional view of the device of FIG. 2A during a state of operation of the device.
Figure 2C:
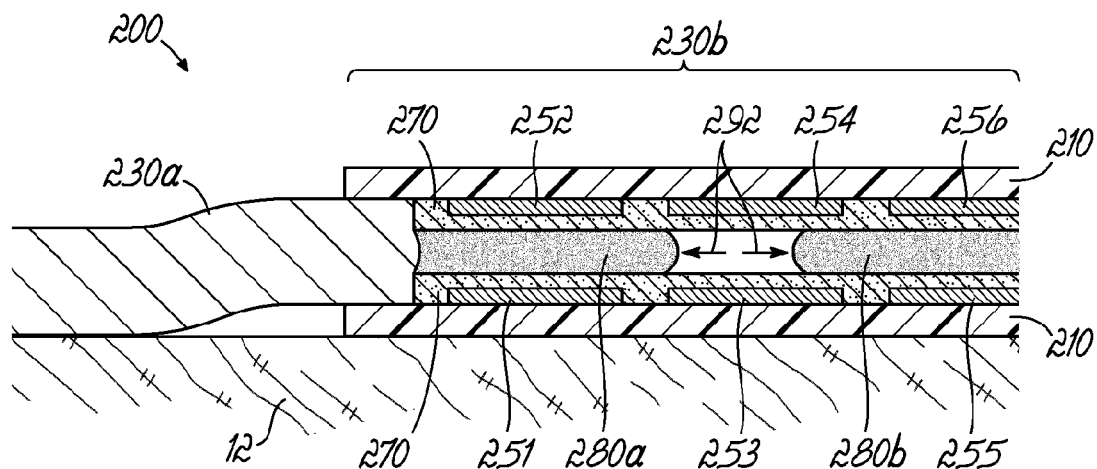
FIG. 2C is a cross-sectional view of the device of FIG. 2A during a state of operation of the device.

With reference to FIGS. 2A-2C, where like numerals refer to like features in previous figures, in an embodiment of the disclosed invention, a device 200 comprises sweat coupling components 230a, 230b, which may, for example, represent components 130a, 130b in FIG. 1B, that are in fluid communication with an analyte-specific sensor (e.g., sensor 120). The sweat coupling component 230a transports or wicks sweat from the skin 12 towards the sweat coupling component 230b. In the illustrated embodiment, sweat coupling component 230a provides passive sweat transport, while sweat coupling component 230b provides active sweat transport. The sweat coupling components 230a, 230b are in fluid communication with each other. Suitable materials for the sweat coupling component 230a include, without limitation, a woven hydrophilic mesh of rayon, a hydrophilic microfluidic channel, or other suitable material, wicking component, etc. that transports sweat away from the skin 12. The sweat coupling component 230a may be strongly wicking (e.g., as strong as paper wicking) because, if it becomes saturated with sweat, it will then have an excess of sweat and allow the sweat coupling component 230b to perform its function as described next.

Still referring to FIG. 2A, the sweat coupling component 230b utilizes the electromechanical effect of electrowetting to transport sweat. The sweat coupling component 230b includes opposing films or substrates 210 that define a fluid channel. Suitable materials for the substrates 210 include, without limitation, polyethylene terephthalate (PET), Kapton®, or other materials suitable for forming a channel. The substrates 210 each carry a plurality of electrodes 251, 252, 253, 254, 255, 256. While six electrodes are shown, with three carried by each substrate 210, it should be recognized that the number of electrodes may vary. To transport sweat via electrowetting, the sweat coupling component 230b includes a hydrophobic dielectric layer 270 that covers the electrodes 251-256. More generally, an embodiment of the disclosed invention may include a sweat coupling component that is coated with at least one hydrophobic material. Suitable materials for the hydrophobic material include, without limitation, Teflon®, an oil, or a hydrophobic fluid immiscible with sweat that creates hydrophobicity by having a low interfacial surface tension with a solid surface that the sweat should not wet (e.g., sweat should have a contact angle of greater than 90 degrees on that surface). As an example, the hydrophobic dielectric layer 270 may be Teflon® having a thickness of about 1 μm, and the electrodes 251-256 may be aluminum having a width on the order of about 1 mm, although the electrodes 251-256 may be larger or smaller. The opposing surfaces of the hydrophobic dielectric layer 270 define a channel with a height h. The height h typically is within a range of several μm (e.g., 10 to 150 μm) to several mm (e.g., 1 mm to 10 mm) and may be, for example, 100 μm. Sweat may be transported to the sweat coupling component 230b by the sweat coupling component 230a but, because this channel is hydrophobic, may not automatically move into the sweat coupling component 230b. As shown in FIG. 2B, if a suitable voltage (e.g., 10 s of V, such as 10 to 80 V) is applied to the electrodes 251-256, sweat 280 is drawn into the channel by electrowetting (arrow 290). Therefore, an embodiment of the disclosed invention may include at least one sweat coupling component that utilizes electrowetting for sample introduction. More generally, an embodiment of the disclosed invention may include at least one sweat coupling component that contains at least one electromechanical component that creates a positive pressure for sample introduction. While electrowetting is described above, embodiments of the disclosed invention may include other electrofluidic mechanisms for pumping and moving fluid including, without limitation, electroosmosis or electrocapillarity.

In an aspect of the disclosed invention, sweat entering the channel may be split into multiple samples. As shown in FIG. 2C, the voltage is removed from at least electrode 254 and 253 to cause splitting of the sweat 280 into discrete samples 280a, 280b (arrows 292). The timing for applying and removing voltages depends on the desired sizes of sweat droplets and on the droplets' fluid surface tensions. Voltage application timing can typically range from several milliseconds to seconds. Sample splitting used as described creates a positive pressure for the sweat sample 280b due to Laplace pressure, which can push the sweat sample 280b further into the device 200, e.g., in a direction towards an analyte-specific sensor. Other known variations of splitting a sample via fluid pumping may be included in an embodiment of the disclosed invention. For example, in an embodiment, a sweat coupling component may utilize a piezoelectric pumping method to move a sweat sample into the lab-on-chip component.

Figure 3A:
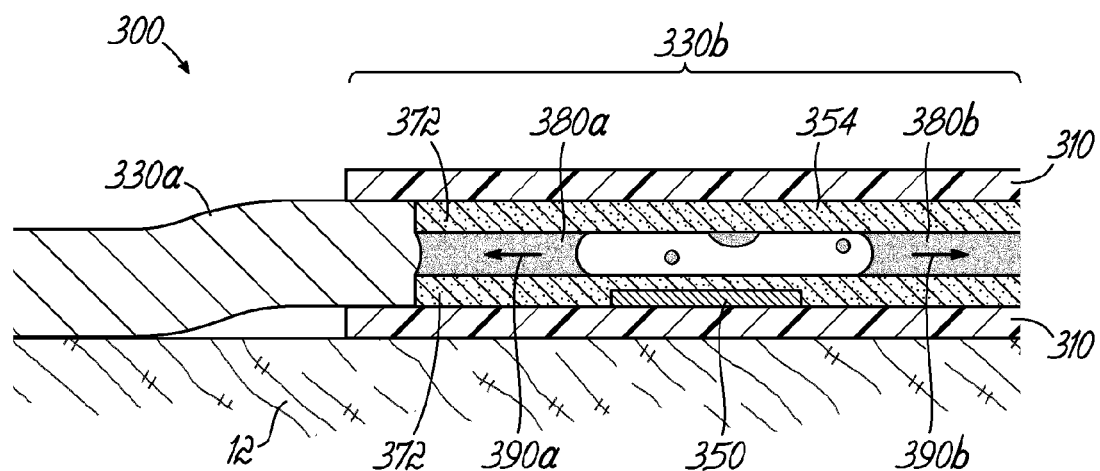
FIG. 3A is a cross-sectional view of a device according to an embodiment of the disclosed invention.
Figure 3B:
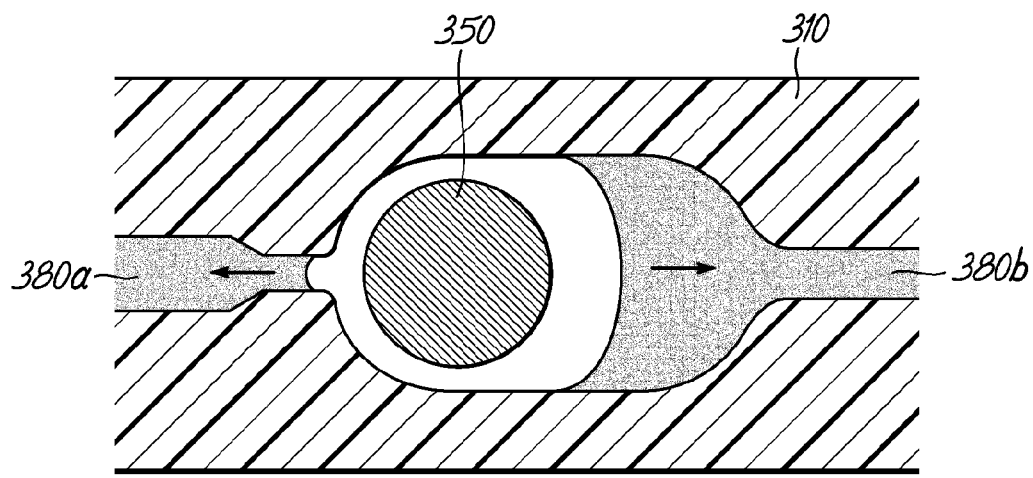
FIG. 3B is a cross-sectional top view of the device of FIG. 3A with the hydrophilic film removed.

With reference to FIGS. 3A and 3B, where like numerals refer to like features in previous figures, in an embodiment of the disclosed invention, a device 300 comprises a unidirectional fluid pump. The device 300 includes sweat coupling components 330a, 330b, which may, for example, represent components 130a, 130b in FIG. 1B. The sweat coupling component 330b includes opposing substrates 310, each covered by a hydrophilic film 372, which defines a fluid channel. Suitable materials for the hydrophilic film 372 include, without limitation, silicon dioxide ($SiO_2$), plasma-treated Kapton®, etc. Because the films 372 are hydrophilic, sweat from the sweat coupling component 330a could readily or constantly be wicking into the fluid channel formed between the surfaces of the film 372. Also within the sweat coupling component 330b, an electrode forms an electrically resistive heater 350, which is covered by the hydrophilic film 372, that is activated by applying a voltage or current across it (additional requisite electrode contacts not shown). Suitable materials for the resistive heater 350 include, without limitation, carbon, gold, etc. As shown in FIGS. 3A and 3B, the applied voltage causes boiling of the sweat 380, which forms gas or vapor in the channel. The formation of the gas or vapor results in movement of the sweat sample 380a in the direction of arrow 390a and movement of the sweat sample 380b in the direction of arrow 390b. In an embodiment, the flow rate associated with movement of the sweat sample 380b is greater than the flow rate of the sweat sample 380a; when the wicking/heating/boiling cycle is repeated, a net flow of discrete samples of the sweat 380 is achieved in the direction of arrow 390b. Thus, the device 300 includes at least one unidirectional pump operated by creation of a gas or vapor. This can be achieved using unidirectional valves, flow resistance (as shown in FIG. 3B where the channel width is the narrowest), or other techniques known to those skilled in the art.

With respect to embodiments of the disclosed invention, many active sweat coupling components could be susceptible to surface fouling, which, for example, may change the hydrophilicity or hydrophobicity of a surface. An embodiment of the disclosed invention may therefore include self-cleaning agents or self-cleaning techniques for at least one surface, including use of oils, such as silicone oils, Isopar® oil, alkanes, surfactants, or other techniques to prevent or mitigate surface fouling. For example, with further reference to FIG. 2A, use of oil along with the hydrophobic dielectric layer 270 in the electrowetting device 200 can significantly reduce fouling of the surface of the hydrophobic dielectric layer 270.

While specific embodiments have been described in detail to illustrate the disclosed invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A device for sensing a first analyte in sweat on skin, comprising:
    an analyte-specific sensor for sensing the first analyte; and
    an active sweat coupling component for transporting at least one sweat sample inside the device and into fluid communication with the analyte-specific sensor;
    wherein the active sweat coupling component includes:
        opposing substrates that define a fluid channel; and
        at least one electrode positioned on at least one of the opposing substrates.

2. The device of claim 1, wherein the active sweat coupling component is configured to create a positive pressure upon the at least one sweat sample.

3. The device of claim 1, further comprising a wicking component.

4. The device of claim 3, wherein the wicking component and the active sweat coupling component are in fluid communication with each other.

5. The device of claim 1, wherein the active sweat coupling component comprises an electrofluidic mechanism.

6. The device of claim 5, wherein the electrofluidic mechanism comprises an electrowetting component.

7. The device of claim 1, wherein the active sweat coupling component comprises an electrofluidic component.

8. The device of claim 1, wherein the active sweat coupling component comprises an electrically driven uni-directional pump.

9. The device of claim 1, wherein the active sweat coupling component includes a hydrophobic coating that defines a fluid channel.

10. The device of claim 1, wherein the active sweat coupling component includes a hydrophilic coating that defines a fluid channel.

11. The device of claim 1, further comprising a self-cleaning agent.

12. A method of sensing a first analyte in sweat on skin, comprising:
    actively transporting at least one sweat sample into fluid communication with an analyte-specific sensor for sensing the first analyte using an active sweat coupling component including opposing substrates that define a fluid channel and at least one electrode positioned on at least one of the opposing substrates; and
    sensing the first analyte using the analyte-specific sensor.

13. The method of claim 12, wherein the active sweat coupling component creates a positive pressure upon the at least one sweat sample in a direction towards the analyte-specific sensor.

14. The method of claim 12, further comprising passively transporting sweat to the active sweat coupling component using a passive sweat coupling component.

15. The method of claim 14, wherein the passive sweat coupling component is a wicking component.

16. The method of claim 14, wherein the passive sweat coupling component and the active sweat coupling component are in fluid communication with each other.

17. The method of claim 12, wherein actively transporting at least one sweat sample comprises electrofluidically transporting the at least one sweat sample.

18. The method of claim 17, wherein actively transporting at least one sweat sample comprises electrowetting.

19. The method of claim 12, wherein actively transporting at least one sweat sample comprises pumping the at least one sweat sample using a uni-directional pump.

20. The method of claim 12, wherein actively transporting at least one sweat sample comprises transporting the at least one sweat sample through a channel defined by a hydrophobic coating.

21. The method of claim 12, wherein actively transporting at least one sweat sample comprises transporting the at least one sweat sample through a channel defined by a hydrophilic coating.

* * * * *